(12) United States Patent
Senzaki et al.

(10) Patent No.: US 7,314,476 B2
(45) Date of Patent: Jan. 1, 2008

(54) BALLOON CATHETER

(75) Inventors: Hideaki Senzaki, Kawagoe (JP); Toshiki Kobayashi, Kawagoe (JP); Katsuya Miyagawa, Osaka (JP); Hideaki Kataoka, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 11/038,773

(22) Filed: Jan. 21, 2005

(65) Prior Publication Data

US 2005/0187574 A1    Aug. 25, 2005

(30) Foreign Application Priority Data

Jan. 22, 2004   (JP)   ............... 2004-014163

(51) Int. Cl.
   *A61M 29/00*   (2006.01)
(52) U.S. Cl. .............. 606/194; 604/103; 604/916
(58) Field of Classification Search .......... 604/96.01, 604/103, 103.03, 103.06, 103.07, 103.09, 604/915–916, 918–921; 606/192–194; 623/1.11
   See application file for complete search history.

(56) References Cited

U.S. PATENT DOCUMENTS

| | | | | |
|---|---|---|---|---|
| 4,963,313 A | * | 10/1990 | Noddin et al. ............... 264/573 |
| 4,994,072 A | * | 2/1991 | Bhate et al. ................. 606/194 |
| 5,192,296 A | * | 3/1993 | Bhate et al. ................. 606/194 |
| 5,308,356 A | * | 5/1994 | Blackshear et al. .......... 606/194 |
| 5,484,409 A | * | 1/1996 | Atkinson et al. ......... 604/103.03 |
| 5,512,051 A | * | 4/1996 | Wang et al. ............ 604/103.14 |
| 6,468,243 B1 | * | 10/2002 | Miyagawa et al. ....... 604/96.01 |
| 6,565,595 B1 | * | 5/2003 | DiCaprio et al. ........... 623/1.11 |
| 6,699,273 B2 | * | 3/2004 | Langan ...................... 623/1.11 |
| 2002/0038141 A1 | * | 3/2002 | Yang et al. ................. 623/1.12 |
| 2002/0082553 A1 | * | 6/2002 | Duchamp .............. 604/103.06 |
| 2002/0183777 A1 | | 12/2002 | Shannon ..................... 606/192 |
| 2006/0135947 A1 | * | 6/2006 | Soltesz et al. .............. 604/516 |

FOREIGN PATENT DOCUMENTS

| | | |
|---|---|---|
| EP | 0 442 657 A2 | 8/1991 |
| EP | 1 121 955 A2 | 8/2001 |
| JP | 10-234860 A | 9/1998 |
| JP | 2002-143311 A | 5/2002 |
| JP | 2003-509175 A | 3/2003 |
| WO | 96/40349 A1 | 12/1996 |
| WO | 00/54829 A2 | 9/2000 |
| WO | 01/21247 A1 | 3/2001 |

* cited by examiner

*Primary Examiner*—Loan H. Thanh
(74) *Attorney, Agent, or Firm*—Kubovcik & Kubovcik

(57) ABSTRACT

A balloon catheter for interatrial septum dehiscence including an expandable and contractible balloon, and a shaft to which the balloon can be attached at the distal end thereof, wherein fixing members are provided at balloon mounting portions to be attached to the shaft. The fixing members are a pair of members in opposed relationship to each other at the ends of the balloon. The pair of members generally has an identical shape.

8 Claims, 9 Drawing Sheets

A-A

BALLOON CATHETER

FIELD OF THE INVENTION

The present invention relates to a balloon catheter used for treatment of congenital heart disease such as tricuspid atresia, pure pulmonary atresia, or complete transposition of great vessels. More specifically, the invention relates to a balloon catheter used for interatrial septum dehiscence.

BACKGROUND OF THE INVENTION

As one of the treatment techniques for congenital heart disease such as tricuspid atresia, pure pulmonary atresia, or complete transposition of great vessels, there is a formation of interatrial traffic. The interatrial traffic generates blood flow between both atrials by opening a hole in an interatrial septum located between a right atrium and a left atrium. By interatrial traffic, hypoxemia and pulmonary congestion are improved.

In the related art, a balloon catheter is used for interatrial septum dehiscence. However, the prior art catheter has a problem that since it is too thick to use for new born infants or nursling babies, application thereof is limited. In actual usage, a patient suffers significant mental and physical stress, since a sheath (sheath introducer), which is used when inserting the catheter into a vessel, is thick.

As a catheter relating to interatrial septum dehiscence, for example, a catheter as disclosed in JP2003-509175 is publicly known.

SUMMARY OF THE INVENTION

It is necessary to reduce the thickness of a balloon for reducing the diameter of the catheter having the conventional shape in order to cope with the above described problems. However, in association with it, various problems such that the expanded diameter of the balloon is insufficient or the strength of the balloon is lowered (resulting in deflection or rupture due to tensile forces) arise.

In view of the circumstances described above, it is an object of the present invention to provide a catheter for interatrial septum dehiscence which can dehisce an interatrial septum reliably and can be used with thinner sheathes without causing problems such as insufficient balloon expansion diameter or lowering of the strength of the balloon (and the resulting deflection or rupture due to tensile forces).

In order to solve the above-described problems, the inventors, after having devoted themselves to study, achieved the present invention from an idea that the diameter of the catheter can be reduced by employing one having a pneumatic balloon at the distal end of a shaft with fixing members attached to the ends of the balloon, and hence the size of the sheath to be applied thereon can also be reduced. In other words, the invention provides a balloon catheter including an expandable and contractible balloon, which has a ball shape when expanded, and a shaft to which the balloon can be attached at the distal end thereof, wherein fixing members are provided at balloon mounting portions to be attached to the shaft. The fixing members are a pair of members in opposed relationship to each other at the ends of the balloon. The pair of members generally has an identical shape.

The portion of the fixing member which comes into contact with the balloon has a constant, or fixed, shape opening widely toward the balloon. The fixing member has a shape which is symmetrical with respect to the axis of the shaft and is disposed so that the axial center thereof matches the axial center of the shaft, and has an outer peripheral surface which is formed into a tapered shape widening toward the balloon. The outer diameter of the fixing members is 0.6 to 2.5 mm. A material forming the fixing members may be a soft material. Furthermore, the material forming the fixing members may be a metallic material. In addition, the material forming the fixing members may be a composite material including a soft material and a metallic material. Still further, the composite material may be a braid tube.

PREFERRED EMBODIMENTS OF THE INVENTION

Figure 1:
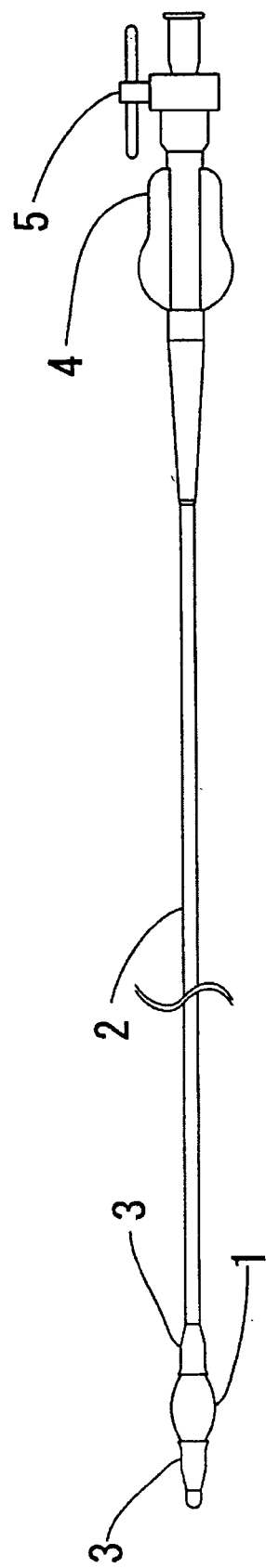
FIG. 1 is a plan view showing an embodiment of the present invention.

Referring now to the drawings, embodiments of the present invention will be described.

As shown in FIG. 1 to FIG. 5, the catheter for interatrial septum dehiscence according to the present invention includes a shaft 2, a pneumatic balloon 1 attached to the distal end of the shaft 2, fixing members 3 for preventing displacement of the balloon 1 (deflection occurring when the balloon 1 is pulled through a hole in the atrial septum) upon expansion of the balloon 1 and for allowing the smooth insertion into and withdrawal from a sheath, a connector 4 attached to the proximal end of the shaft 2, and a two-directional turncock 5.

The shaft 2 can be inserted into a vessel via a sheath (not shown) from a femoral vein, and has a hardness to an extent that does not cause damage in the vein. The shaft 2 has a circular shape or a similar shape, and preferably has a diameter of 0.5 to 2 mm. A lumen (not shown) for delivering physiological saline that expands the balloon 1 is provided on the shaft 2, and the number of lumens is determined as needed. The shaft 2 may be a double-lumen or a dual tube including a lumen for a guide wire. Materials of the shaft 2 that may be employed are plastics such as polyolefin, polyamide, polyester, fluorine containing resin, silicone resin, polyvinyl chloride, polyurethane, or natural rubber, stainless steel, or a braid tube including a combination of plastic and stainless steel. The wall thickness of the balloon is typically in the range of about 0.1 to 0.5 mm and is, preferably, about 0.2 mm.

The balloon 1 can be expanded to a size that dehisces the interatrial septum. Since the expanded diameter required for dehiscence is 30 mm at the maximum, the outer diameter thereof is preferably 2 to 5 mm, and the extension in the expanded state is preferably about five to eight times. As materials for forming the balloon 1, synthetic rubber such as silicone rubber or polyisoprene, or natural rubber may be employed.

Mounting of the balloon 1 to the shaft 2 can be performed by bonding both ends of the balloon 1 with, for example, a cyanoacrylate or silicone adhesive agent.

The fixing members 3, serving to prevent displacement of the balloon 1 when the balloon is expanded (deflection occurring when the balloon 1 is pulled through a hole in the atrial septum) and to enable smooth insertion into and withdrawal from the sheath, are disposed at the mounting portions between both ends of the balloon 1 and the shaft 2.

Each of the fixing members has an axial length of about 3 to 20 mm and, preferably, about 5 to 10 mm. The fixing members each cover a portion of the length of the balloon at its respective ends. The total of the portions of the length of the balloon covered by the fixing members is about 5 to 50% of the overall length of the balloon. The length of the balloon between and not covered by the fixing members is about 3 to 30 mm and, preferably, about 10 to 20 mm.

Subsequently, the fixing members 3 will be described in detail. The fixing members 3 are a pair of members in opposed relationship to each other at the ends of the balloon. Since the fixing members 3 are disposed so as to oppose to each other at the ends of the balloon 1, displacement of the balloon 1 when the balloon 1 is expanded can be reliably prevented. The pair of fixing members 3 has the same shape, and are standardized, thereby achieving cost reduction. In addition, the contact portions of the fixing members 3 with respect to the balloon 1 have a widening (or flared) shape 31 widening toward the balloon. Therefore, the balloon 1 in an expanded state can be stably and reliably held by the large contact portions, and displacement of the balloon can be prevented.

In addition, the fixing member 3 has a shape that is symmetrical with respect to the axis of the shaft 2 and is disposed so that the axial center thereof matches the axial center of the shaft 2, and has an outer peripheral surface which is formed into a tapered shape 32 widening toward the balloon 1. Therefore, not only insertion into and withdrawing from the sheath can be smooth, but also the fixing member 3 is prevented from being stuck to the peripheral tissues when it moves within the body, whereby tissue is prevented from becoming damaged even when the fixing member 3 touches the peripheral tissue. The fixing member 3 may be disposed as only one single piece at one end. The fixing members 3 may have different shapes in such a manner that the tapered shape 32 of one of the fixing members 3 is elongated at the distal end with respect to the other one in order to further smoothen, or facilitate insertion into the body.

The fixing member 3 is preferably 0.6 to 2.5 mm in largest outer diameter for coordinating with the size of the shaft 2 or the sheath size to be applied. Materials for forming the fixing members 3 that can be employed are soft materials such as plastics such as polyolefins, polyamides, polyesters, fluorine containing resins, silicone resin, polyvinyl chloride, polyurethanes, or natural rubber. With the employment of a soft material, light-weight and flexibility of the fixing member may be expected.

In addition, metallic materials having high corrosion resistance, such as stainless steel, can be employed. With the use of a metallic material, strength of the fixing members is improved. Furthermore, composite materials combining a soft material and a metallic material obtained by embedding a metallic material such as stainless steel wires in a net shape into a plastic soft material, for example, a braid tube, may be employed. With the use of the composite material, flexibility and strength can be well balanced in the fixing members.

Mounting of the fixing member 3 may be performed by bonding with, for example, a cyanoacrylate or silicone adhesive agent, or by fixing by thermal welding or with a thermal contraction tube.

Figure 2:
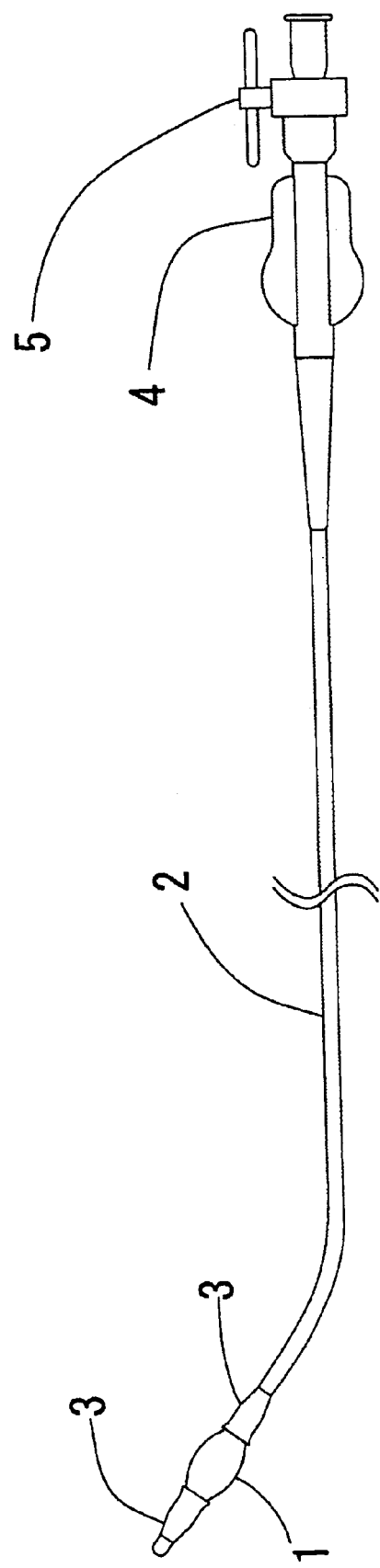
FIG. 2 is a plan view showing another embodiment of the present invention.
Figure 3:
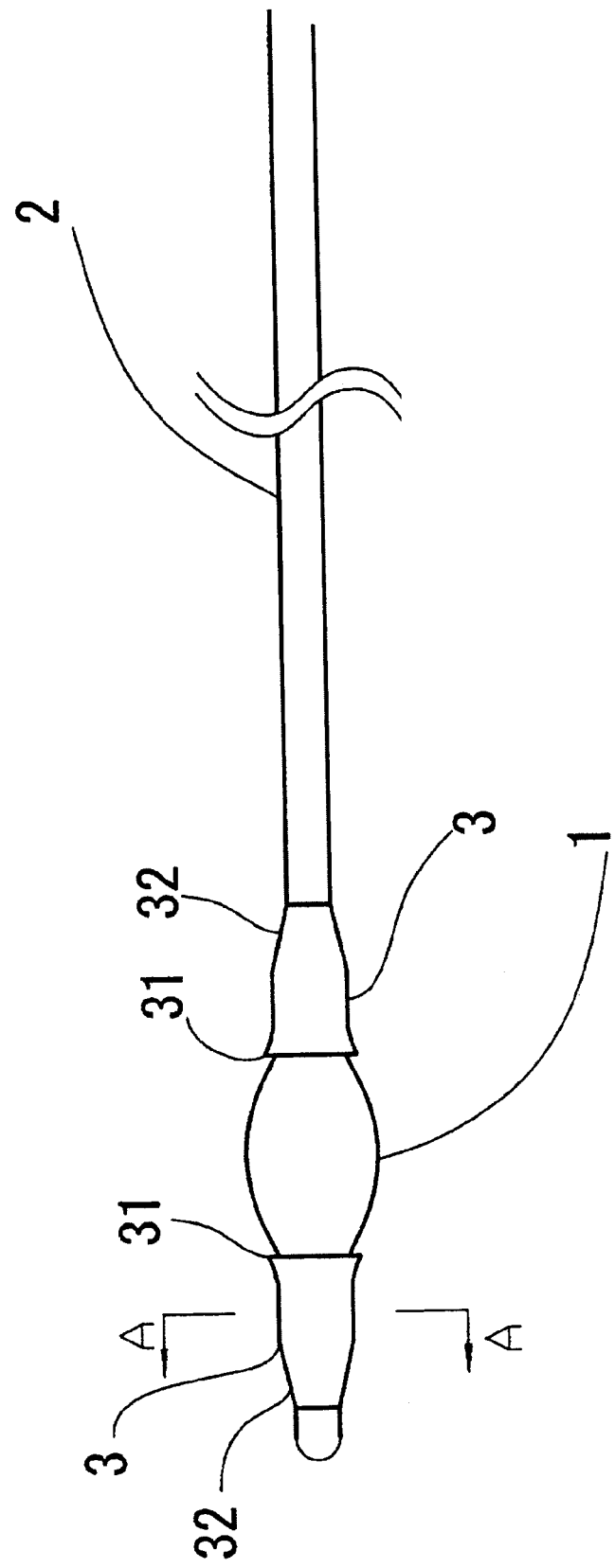
FIG. 3 is an enlarged view of a distal portion including a balloon and fixing members.
Figure 4:
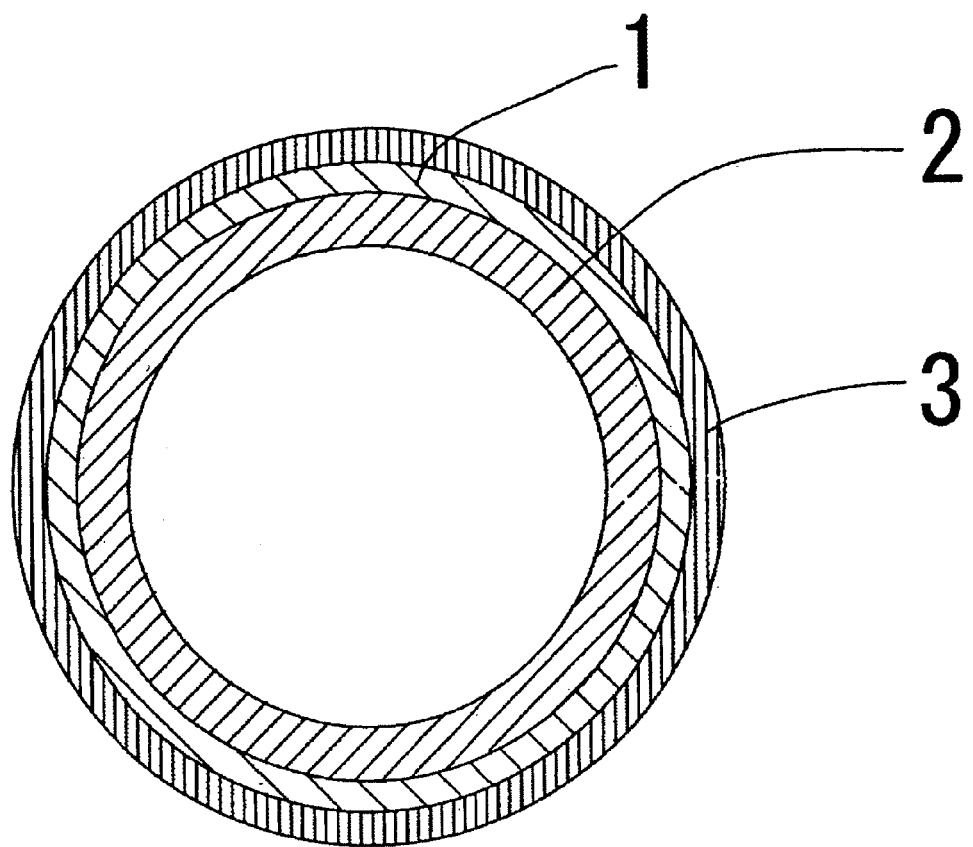
FIG. 4 is an enlarged cross sectional view taken along the line A-A in FIG. 3.
Figure 5:
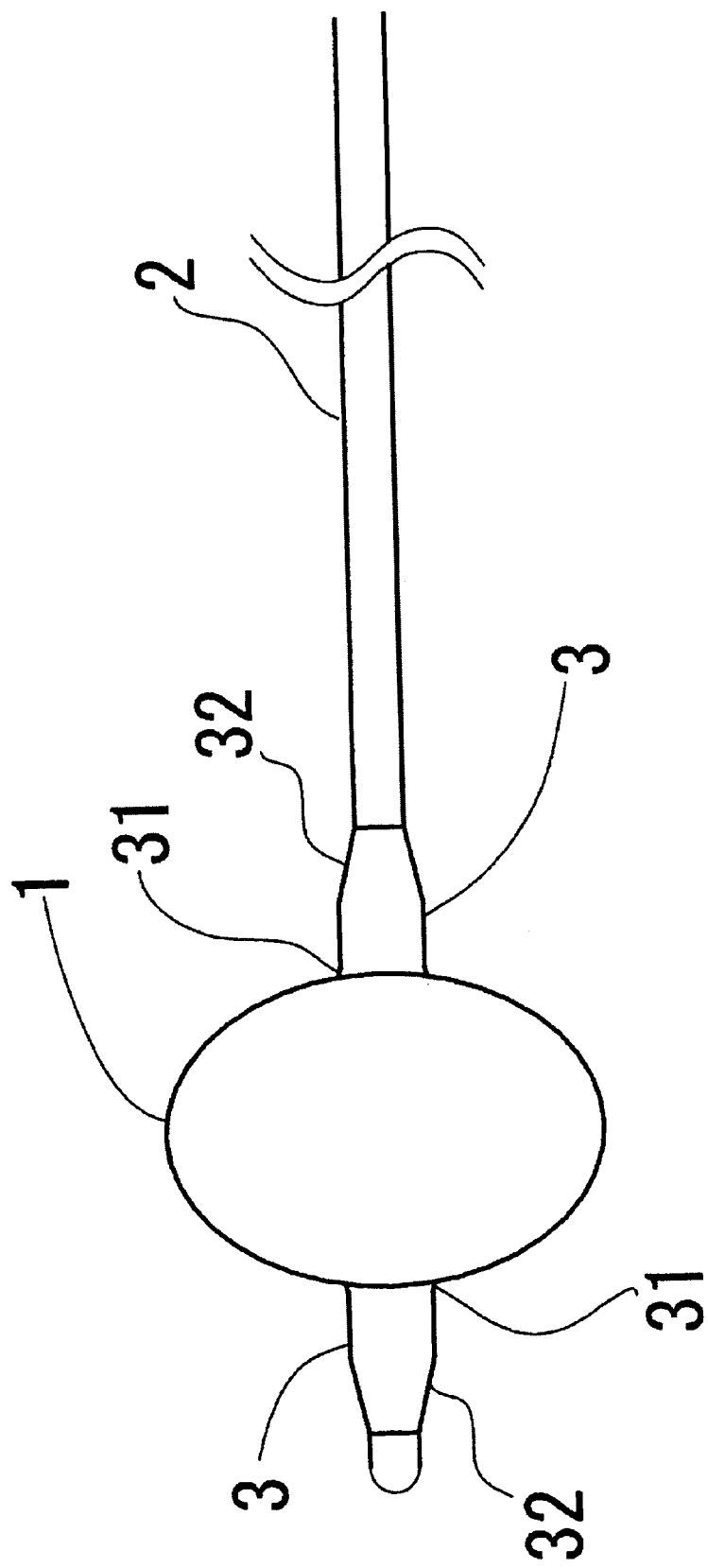
FIG. 5 is a drawing showing a state in which the balloon is expanded in FIG. 3.

The catheter may be bent at the distal end of the shaft 2 by 30 to 40 degrees according to the position of the interatrial septum dehiscence as shown in FIG. 2.

Subsequently, referring to the drawings (FIG. 6 to FIG. 9), interatrial septum dehiscence using the catheter for interatrial septum dehiscence according to the present invention will be described.

Figure 6:
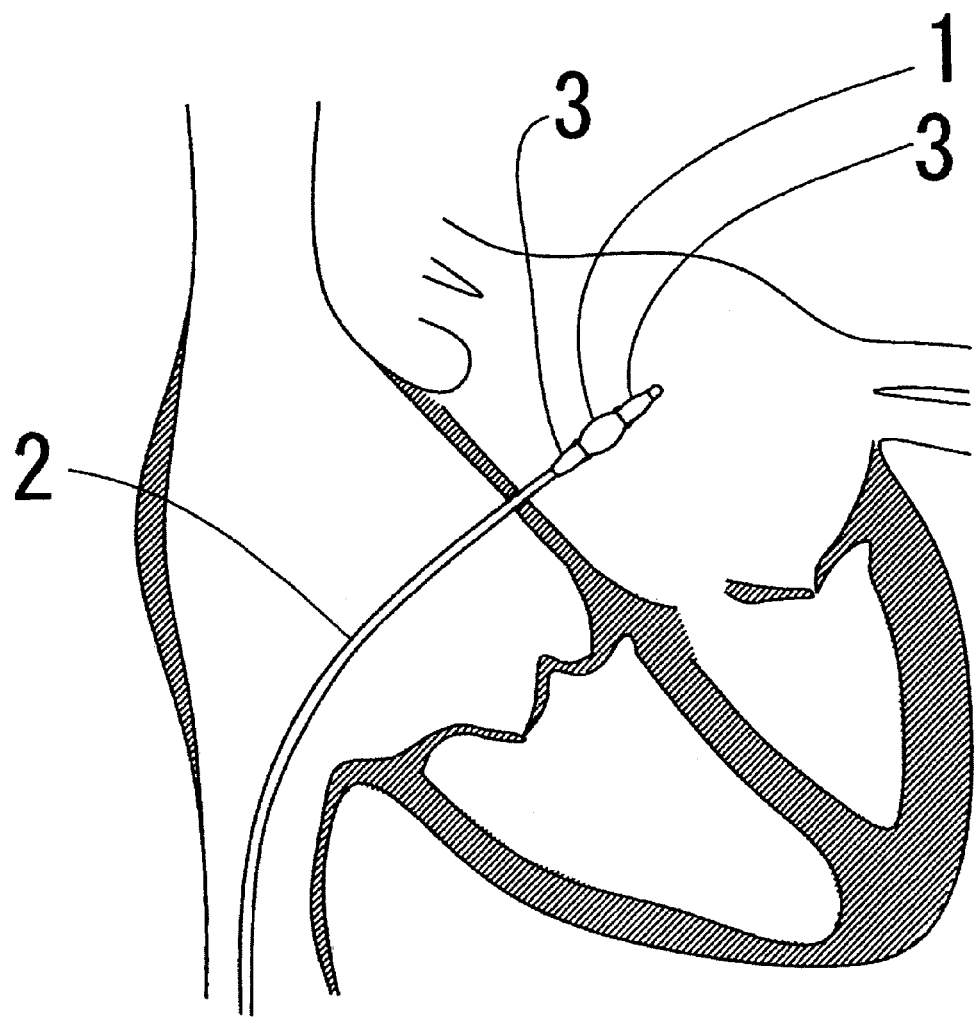
FIG. 6 is an explanatory drawing illustrating a step of interatrial septum dehiscence using a catheter for interatrial septum dehiscence of the present invention.
Figure 7:
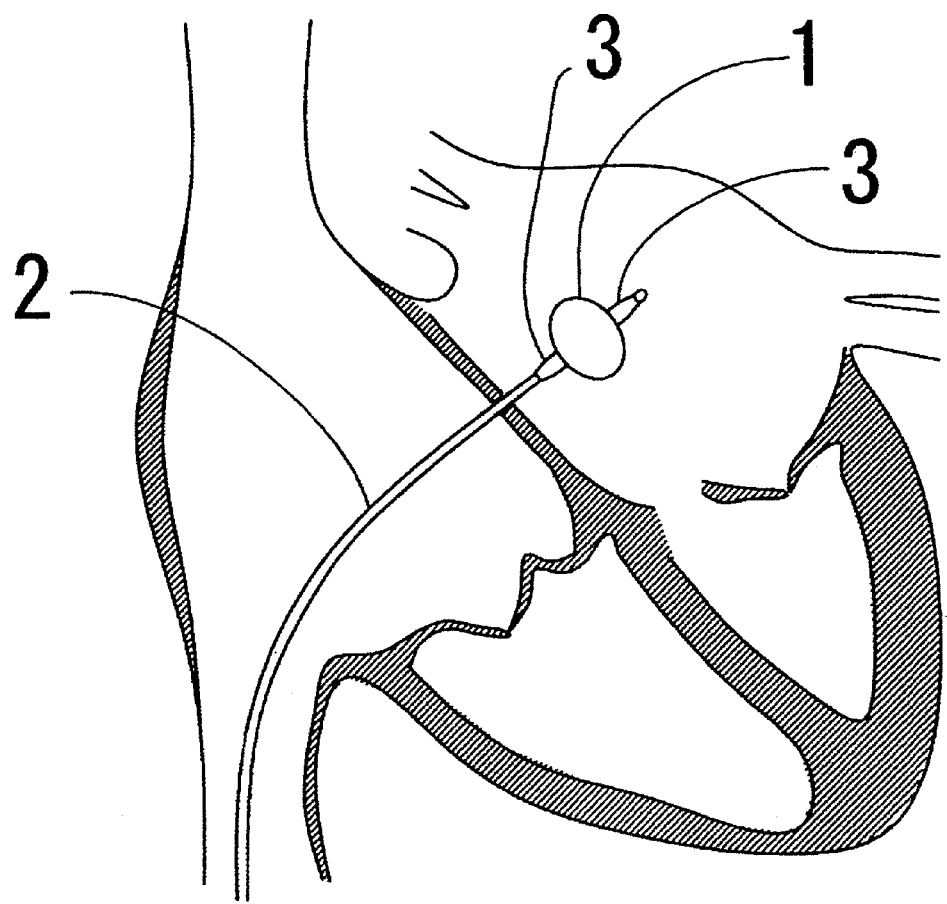
FIG. 7 is an explanatory drawing illustrating a step of interatrial septum dehiscence using a catheter for interatrial septum dehiscence of the present invention.
Figure 8:
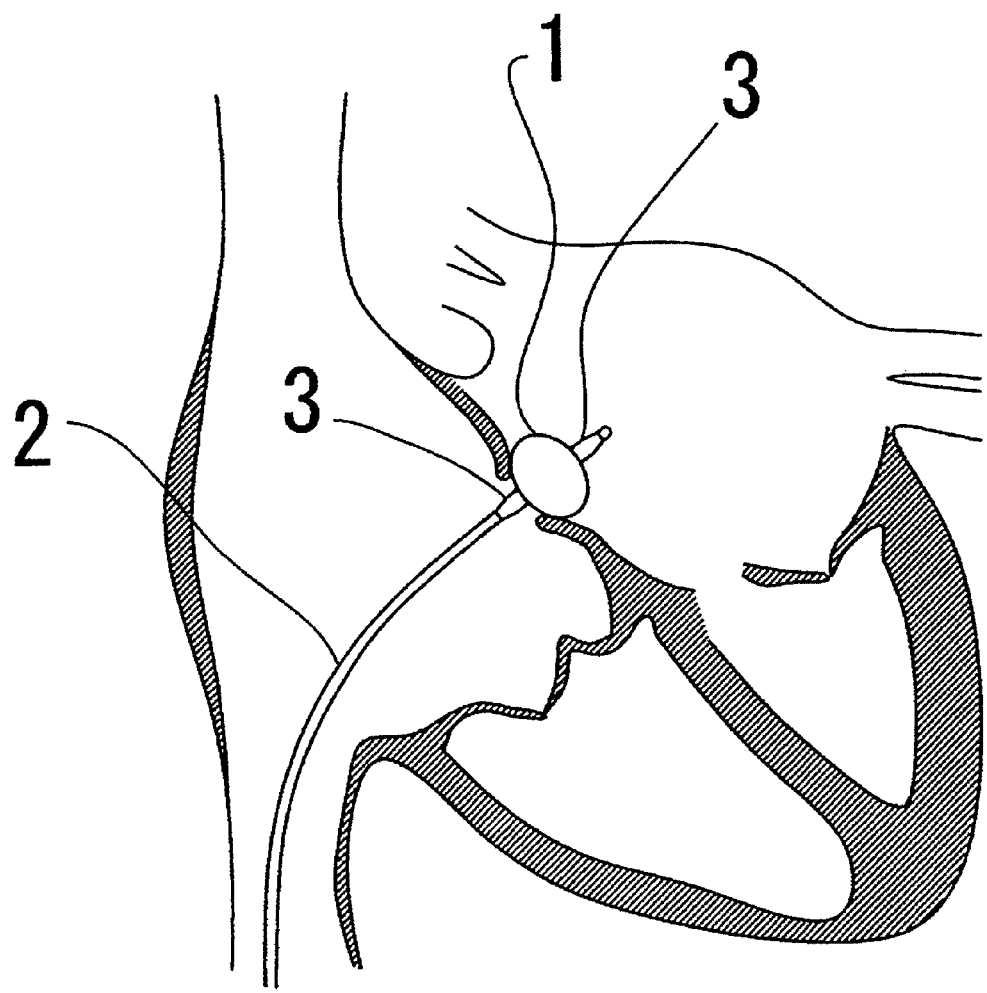
FIG. 8 is explanatory drawing illustrating a step of interatrial septum dehiscence using a catheter for interatrial septum dehiscence of the present invention.
Figure 9:
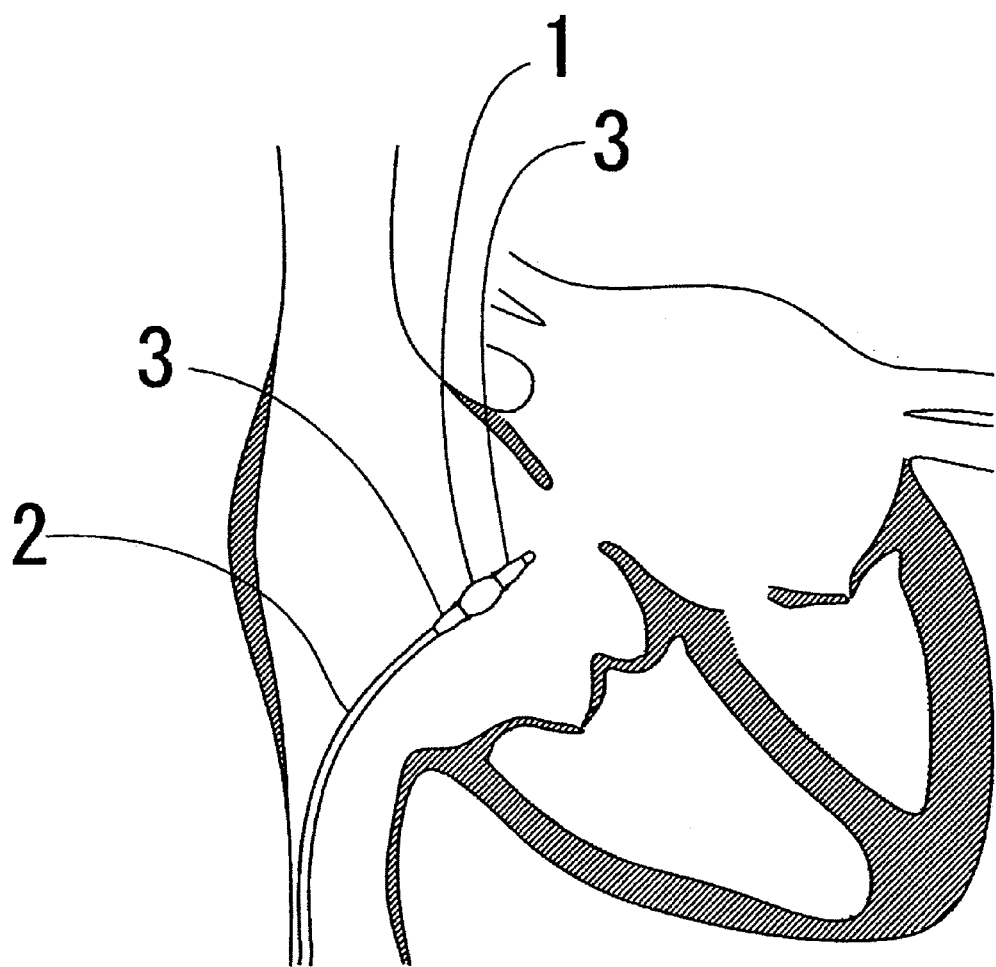
FIG. 9 is explanatory drawing illustrating a step of interatrial septum dehiscence using a catheter for interatrial septum dehiscence of the present invention.

In a first place, a catheter for interatrial septum dehiscence as shown in FIG. 1 is provided, the balloon 1 is inserted from a femoral vein in a state in which the balloon 1 is kept sufficiently at a negative pressure, and the distal end of the shaft 2 including the balloon 1 is introduced through a fine hole on the interatrial septum into the left atrial (see FIG. 6). After having checked the position, physiologic saline containing, for example, contrast agent is injected into the balloon 1 through a lumen (not shown) to expand the balloon 1 (see FIG. 7). After having expanded the balloon 1 to a target size, the catheter is pulled and the balloon 1 is withdrawn so as to extend the fine hole on the interatrial septum (FIG. 8). When the balloon 1 is withdrawn into the right atrial and formation of a hole having a sufficient size is confirmed, the physiological saline containing contrast agent is taken out from the balloon 1, and the balloon 1 is brought into a sufficiently negative pressure state as it was when being inserted (FIG. 9). Finally, the catheter for interatrial septum dehiscence is taken out of the body to complete the interatrial septum dehiscence.

INDUSTRIAL APPLICABILITY

With the employment of the present invention, the problems such as insufficient balloon expansion diameter or lowering of the strength of the balloon (and the resulting deflection or rupture due to tensile forces) are avoided, and a thinner sheath can be used in catheter operation, so that the range of patients to whom the catheter operation can be applied increases, and mental and physical stress suffered by the patients can be alleviated, whereby the interatrial septum dehiscence can easily be performed.

Since the contact portions between the fixing member and the balloon have a shape widening toward the balloon, the balloon in an inflated state can be stably and reliably held by large contact portions and displacement of the balloon can be prevented. In addition, since the outer peripheral surface of the fixing member has a tapered shape widening toward the balloon, not only insertion into and withdrawing from the sheath are smoothened, but also tissues may be prevented from becoming damaged even when the fixing member touches peripheral tissues during movement within the body.

Soft materials such as plastic or natural rubber, metallic materials such as stainless steel, and composite materials such as a braid tube may be employed for the fixing member. Therefore, it is possible to increase the flexibility or strength, and furthermore, to freely adjust an increase in flexibility or strength of the fixing member.

This application claims priority based on Japanese Patent Application No. 2004-014163, which is incorporated herein by reference.

What is claimed is:

1. A balloon catheter comprising an expandable and contractible balloon having mounting portions at ends thereof and an expandable and contractible portion between said mounting portions, said expandable and contractible balloon having a ball shape when expanded, a shaft to which the mounting portions of the balloon are attached at the distal end of the shaft, and two fixing members provided one each at the balloon mounting portions attached to the shaft for preventing displacement of the balloon upon expansion of the balloon, wherein the fixing members are a pair of members in opposed relationship to each other and the ends of the balloon, each fixing member having a distal end adjacent the expandable and contractible portion of the balloon and a proximal end at each mounting portion of the balloon, the distal end of each fixing member having a constant shape flaring outwardly at the distalmost end thereof toward the expandable portion of the balloon and contacting the expandable portion of the expandable and contractible balloon when the balloon is expanded, wherein the size of the fixing members do not change upon the change in size of the balloon and wherein each fixing member has a shape which is symmetrical with respect to the axis of the shaft and is disposed so that the axial center thereof matches the axial center of the shaft, and the proximal ends have an outer peripheral surface which is formed into a tapered shape widening toward the balloon.

2. A balloon catheter according to claim 1, wherein the pair of members has an identical shape.

3. A balloon catheter according to claim 1, wherein the largest outer diameter of the fixing member is 0.6 to 2.5 mm.

4. A balloon catheter according to claim 1, wherein a material forming at least one fixing member is a soft material.

5. A balloon catheter according to claim 1, wherein the material forming at least one fixing member is a metallic material.

6. A balloon catheter according to claim 1, wherein the material forming at least one fixing member is a composite material including a soft material and a metallic material.

7. A balloon catheter according to claim 6, wherein the composite material is a braid tube.

8. The balloon catheter according to claim 1, wherein said expandable and contractible balloon 1 has a diameter of 2 to 5 mm and an extension in the expanded state of five to eight times and is made of silicone rubber, polyisoprene or natural rubber.

\* \* \* \* \*